United States Patent
Loescher et al.

(10) Patent No.: US 8,143,466 B2
(45) Date of Patent: Mar. 27, 2012

(54) PROCESS FOR BENZENE REMOVAL FROM GASOLINE

(75) Inventors: Mitchell E. Loescher, Houston, TX (US); Gary G. Podrebarac, Houston, TX (US); Quoc T. Phan, Pearland, TX (US)

(73) Assignee: Catalytic Distillation Technologies, Pasadena, TX (US)

( * ) Notice: Subject to any disclaimer, the term of this patent is extended or adjusted under 35 U.S.C. 154(b) by 532 days.

(21) Appl. No.: 12/368,621

(22) Filed: Feb. 10, 2009

(65) Prior Publication Data

US 2009/0211943 A1   Aug. 27, 2009

Related U.S. Application Data

(60) Provisional application No. 61/031,603, filed on Feb. 26, 2008, provisional application No. 61/114,704, filed on Nov. 14, 2008.

(51) Int. Cl.
*C07C 2/66* (2006.01)

(52) U.S. Cl. .................... 585/467; 585/469; 203/DIG. 6

(58) Field of Classification Search .................. 585/467, 585/469; 203/DIG. 6
See application file for complete search history.

(56) References Cited

U.S. PATENT DOCUMENTS

| | | |
|---|---|---|
| 4,008,290 A | 2/1977 | Ward |
| 4,302,356 A | 11/1981 | Smith, Jr. |
| 4,371,714 A | 2/1983 | Young |
| 4,443,559 A | 4/1984 | Smith, Jr. |
| 4,469,908 A | 9/1984 | Burress |
| 4,731,229 A | 3/1988 | Sperandio et al. |
| 4,891,458 A | 1/1990 | Innes et al. |
| 4,950,823 A * | 8/1990 | Harandi et al. .............. 585/322 |
| 5,003,119 A | 3/1991 | Sardina et al. |
| 5,073,236 A | 12/1991 | Gelbein et al. |
| 5,080,871 A | 1/1992 | Adams et al. |
| 5,087,784 A | 2/1992 | Primack et al. |
| 5,118,872 A | 6/1992 | Smith, Jr. et al. |
| 5,118,897 A | 6/1992 | Khonsari et al. |
| 5,210,348 A * | 5/1993 | Hsieh et al. ................... 585/253 |
| 5,266,546 A | 11/1993 | Hearn |
| 5,386,072 A | 1/1995 | Cozzi et al. |
| 5,431,890 A | 7/1995 | Crossland et al. |
| 5,504,259 A | 4/1996 | Diebold et al. |
| 5,730,843 A | 3/1998 | Groten et al. |
| 5,902,917 A | 5/1999 | Collins et al. |
| 5,998,684 A | 12/1999 | Ho et al. |
| 7,038,100 B2 | 5/2006 | Dandekar et al. |
| 7,297,829 B2 | 11/2007 | Dandekar et al. |

OTHER PUBLICATIONS

International Search Report with Written Opinion for related Application No. US/2009/035059 dated Aug. 24, 2009. (12 pages).

* cited by examiner

*Primary Examiner* — Thuan Dinh Dang
(74) *Attorney, Agent, or Firm* — Osha • Liang LLP

(57) ABSTRACT

A process for the reduction of benzene in a gasoline stream, the process including: feeding a gasoline fraction including benzene and $C_{6+}$ hydrocarbons and at least one of an alcohol and an ether to a catalytic distillation column comprising at least one reaction zone containing an alkylation catalyst, wherein the at least one reaction zone is above a gasoline fraction feed location; concurrently in the catalytic distillation column: separating the $C_6$ hydrocarbons from $C_{7+}$ hydrocarbons, wherein the $C_6$ hydrocarbons and benzene distill upward into the at least one reaction zone; contacting benzene and the at least one of an alcohol and an ether in the at least one reaction zone in the presence of the alkylation catalyst to convert at least a portion of the benzene and alcohol/ether to an alkylate; recovering an overheads fraction including $C_6$ hydrocarbons, any unreacted alcohol and ether, and water; and recovering a bottoms fraction including $C_{7+}$ hydrocarbons and the alkylate.

19 Claims, 1 Drawing Sheet

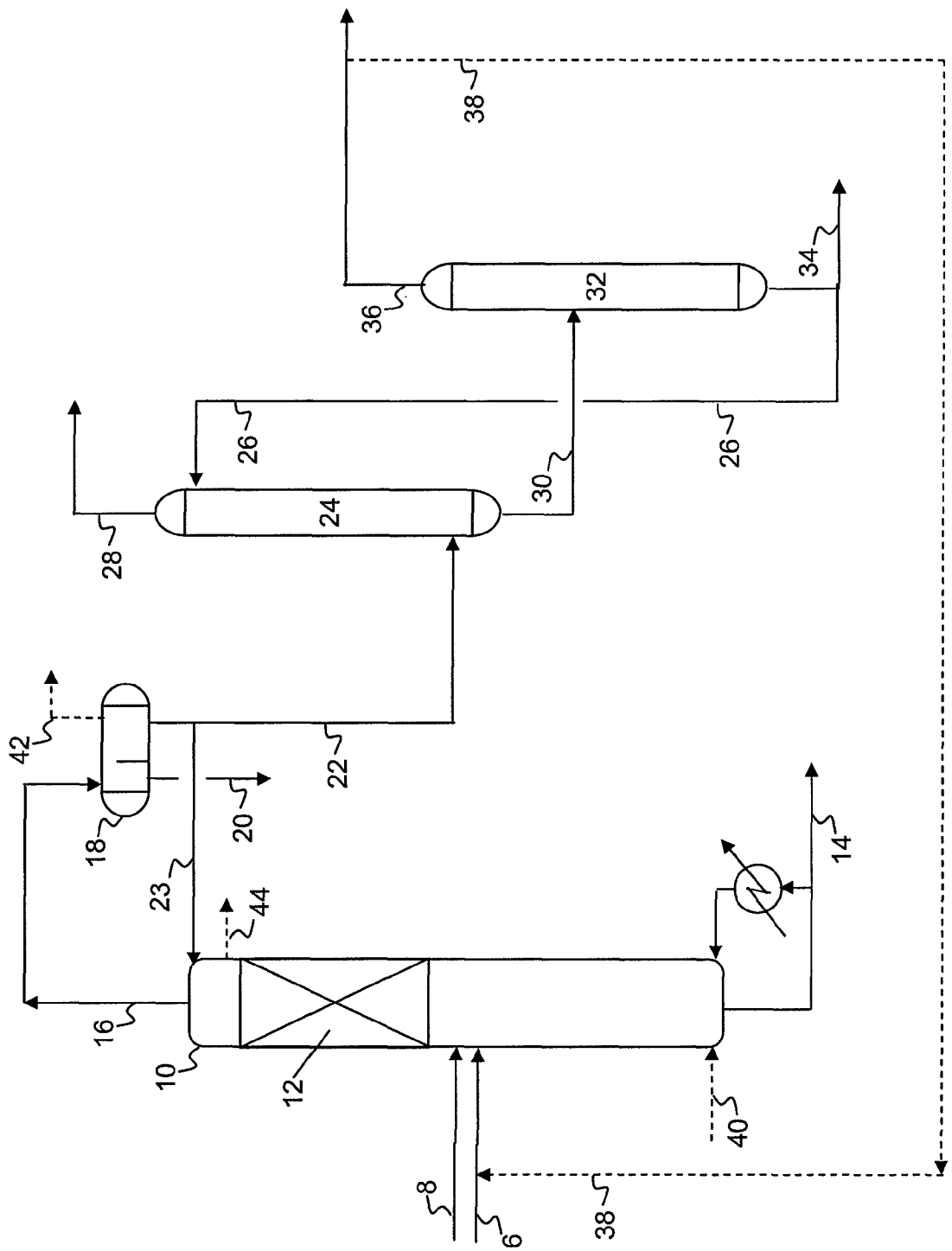

PROCESS FOR BENZENE REMOVAL FROM GASOLINE

CROSS-REFERENCE TO RELATED APPLICATIONS

This application, pursuant to 35 U.S.C. §119(e), claims priority to U.S. Provisional Application Ser. Nos. 61/031,603, filed Feb. 26, 2008, and 61/114,704, filed Nov. 14, 2008, each of which is incorporated by reference in its entirety.

BACKGROUND OF DISCLOSURE

1. Field of the Disclosure

Embodiments disclosed herein relate generally to a process for the reduction or removal of benzene in a gasoline fraction. More specifically, embodiments disclosed herein relate to the removal of benzene from a reformate stream. Removal of benzene may be accomplished via the alkylation of benzene with an alcohol or an ether via catalytic distillation.

2. Background

The demand for cleaner and safer transportation fuels is becoming greater every year. Two major sources of gasoline feedstock, including reforming and catalytic cracking, present both a problem meeting strict environmental regulations and impose certain health risks. For example, light reformate typically contains unacceptably high levels of benzene, a known carcinogen.

Refiners in the U.S. and in other countries are required to remove benzene from reformate streams and other gasoline fractions. Various options for the removal of benzene from such streams may include distillation, extraction, hydrogenation, alkylation, and transalkylation. However, due to the low concentrations of benzene in these streams or a limited quantity of benzene contained in reformate and other streams, it may be uneconomical for a non-integrated refiner to recover benzene from various gasoline fractions, such as reformate, for example. In addition, the refiner may not have access to a market into which he might sell the benzene.

Extraction of benzene requires expensive capital investment in necessary equipment and a customer for the benzene product, neither of which may be feasible for a small, non-integrated refiner. Also, while it is possible to extract benzene from the gasoline pool by fractionation techniques, such techniques are not preferred, because the boiling point of benzene is too close to that of some of the more desirable organic components, including $C_6$ paraffins and isoparaffins. Monoalkylate aromatics (monoalkylate), such as toluene, xylenes, and ethylbenzene are more desirable for gasoline blending, as opposed to benzene, because they are less objectionable both from an environmental and a safety point of view. Additionally, toluene, xylenes, and ethylbenzene each have a higher octane rating than benzene.

Alternatively, benzene in reformate may be removed via hydrogenation. However, hydrogenation of aromatics, such as benzene, results in reduced octane rating and thus diminishes the overall value of the fuel. As with extraction, hydrogenation of benzene also may not be feasible for a small refiner due to the potentially uneconomical costs of supplying hydrogen.

Alkylation of benzene with an olefin to form a monoalkylate product is another option available to refiners. Various processes for the alkylation of benzene are described in, for example, U.S. Pat. Nos. 4,371,714, 4,469,908, 5,118,897, 5,080,871, 5,118,872, 4,891,458, 4,008,290, 5,003,119, 5,902,917, 5,998,684, 5,087,784, 7,038,100, and 7,297,829, among others.

Alkylation processes, such as those mentioned above, in general, may not be as effective in upgrading the overall fuel value of reformate, largely due to the production of polyalkylate by-products. Also, alkylation may require a readily available olefin source, and therefore may not be feasible for small refiners.

Accordingly, there is still a significant need in the art for economical methods to reduce the levels of benzene in refinery streams, especially for smaller, non-integrated refining operations.

SUMMARY OF THE DISCLOSURE

In one aspect, embodiments disclosed herein relate to a process for the reduction of benzene in a gasoline stream, the process including: feeding a gasoline fraction including benzene and $C_{6+}$ hydrocarbons and at least one of an alcohol and an ether to a catalytic distillation column comprising at least one reaction zone containing an alkylation catalyst, wherein the at least one reaction zone is above a gasoline fraction feed location; concurrently in the catalytic distillation column: separating the $C_6$ hydrocarbons from $C_{7+}$ hydrocarbons, wherein the $C_6$ hydrocarbons and benzene distill upward into the at least one reaction zone; contacting benzene and the at least one of an alcohol and an ether in the at least one reaction zone in the presence of the alkylation catalyst to convert at least a portion of the benzene and alcohol or ether to an alkylate; recovering an overheads fraction including $C_6$ hydrocarbons, any unreacted alcohol and/or ether, and water; and recovering a bottoms fraction including $C_{7+}$ hydrocarbons and the alkylate.

Other aspects and advantages will be apparent from the following description and the appended claims.

BRIEF DESCRIPTION OF DRAWINGS

FIG. 1 is a simplified flow diagram of a process for the reduction or removal of benzene from gasoline according to embodiments disclosed herein.

DETAILED DESCRIPTION

In one aspect, embodiments herein relate to processes for the reduction or removal of benzene in a gasoline fraction. More specifically, embodiments disclosed herein relate to the removal of benzene from a reformate stream. Removal of benzene may be accomplished via the alkylation of benzene with at least one of an alcohol and an ether via catalytic distillation.

Alkylation of benzene with an alcohol may be represented by the following reactions. Alkylation of benzene with other alcohols may proceed in a similar manner, producing water and the corresponding alkylate.

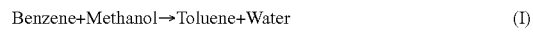

Benzene+Methanol→Toluene+Water    (I)

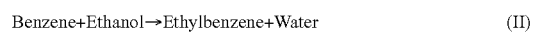

Benzene+Ethanol→Ethylbenzene+Water    (II)

Alkylation of benzene with an ether may be represented by the following reactions. Alkylation of benzene with other ethers may proceed in a similar manner, producing water and the corresponding alkylate.

Benzene+Dimethyl ether→Toluene+Water    (III)

Benzene+Diethyl ether→Ethylbenzene+Water    (IV)

Within the scope of this application, the expression "catalytic distillation reactor system" denotes an apparatus in which the catalytic reaction and the separation of the products take place at least partially simultaneously. The apparatus may comprise a conventional catalytic distillation column reactor, where the reaction and distillation are concurrently taking place at boiling point conditions, or a distillation column combined with at least one side reactor, where the side reactor may be operated as a liquid phase reactor or a boiling point reactor. While both catalytic distillation reactor systems described may be preferred over conventional liquid phase reaction followed by separations, a catalytic distillation column reactor may have the advantages of decreased piece count, reduced capital cost, increased catalyst productivity per pound of catalyst, efficient heat removal (heat of reaction may be absorbed into the heat of vaporization of the mixture), and a potential for shifting equilibrium. Divided wall distillation columns, where at least one section of the divided wall column contains a catalytic distillation structure, may also be used, and are considered "catalytic distillation reactor systems" herein.

While removal of benzene is a primary goal of the processes disclosed herein, it may also be desirable to limit the amount of by-products that may be formed, such as polyalkylate. Refinery hydrocarbon streams containing benzene often contain additional aromatic compounds having a high octane value, such as toluene, ethylbenzene, and the like. Use of catalytic distillation according to embodiments disclosed herein may provide for the selective alkylation of benzene, avoiding or minimizing the undesirable alkylation of the high octane value aromatics, such as toluene, ethylbenzene, etc.

Selective alkylation of benzene via catalytic distillation may be attained by feeding at least one of an alcohol and an ether and a benzene-containing gasoline fraction to a catalytic distillation column including at least one reaction zone containing an alkylation catalyst, where the at least one reaction zone is located in an upper portion of the catalytic distillation column. The benzene-containing gasoline fraction may be fed to the catalytic distillation column at a location below the reaction zone, such that $C_6$ and lighter components, including benzene, may distill upward into the reaction zone. The $C_7$ and heavier components, including toluene, may be distilled downward, avoiding or minimizing contact of $C_{7+}$ aromatic compounds with the alkylation catalyst. The benzene and alcohol or ether may then react to form alkylate and water, where the alkylate product may be recovered with the $C_7$ and heavier components as a bottoms fraction. Water and the $C_6$ and lighter hydrocarbons, including unreacted ethers and alcohols, may be recovered as an overheads fraction.

As known to one skilled in the art, process upsets may result in the unintentional introduction of $C_{7+}$ aromatics to the alkylation reaction zone. In other embodiments, the introduction of $C_{7+}$ aromatics to the alkylation zone may be intentional. For example, it may be desired to alkylate toluene with methanol to form xylenes in some embodiments.

The operation of the catalytic distillation column should be such that reaction conditions suitable for the alkylation of benzene with an alcohol are achieved in the reaction zones. In some embodiments, the reaction zones may be maintained at a temperature in the range from 200° F. to 700° F.; from 200° F. to 400° F. in other embodiments. The overhead pressure of the column will vary depending upon the reaction temperature, and should be maintained so as to attain the desired $C_6/C_7$ split for the selective alkylation of benzene and/or toluene.

The mole ratio of alcohol to benzene fed to the reactor may range from 0.1:1 to 10:1 in some embodiments; from 0.5:1 to 5:1 in other embodiments; from 0.8:1 to 2:1 in other embodiments; and from 0.9:1 to 1.1:1 in other embodiments.

As noted above, the reaction of ethers and benzene also produces water. This is a result of the first alkylation producing a benzene alkylate and an alcohol, where the alcohol may additionally react with benzene to form a second benzene alkylate and water. As such, the mole ratio of ether to benzene fed to the reactor may be the same or lower than the range presented above for the alcohols. In some embodiments, the mole ratio of ether to benzene fed to the reactor may range from 0.05:1 to 10:1 in some embodiments; from 0.1:1 to 5:1 in other embodiments; from 0.4:1 to 1:1 in other embodiments; and from 0.5:1 to 1:1 in other embodiments.

Selective alkylation of benzene as described above may effectively reduce or eliminate benzene in the overheads fraction. In some embodiments, the recovered overheads fraction may contain 0.5 percent or less benzene, by weight. In other embodiments, the benzene content of the recovered overheads fraction may be 0.25 percent or less; 1000 ppm or less in other embodiments; 100 ppm or less in other embodiments; and 10 ppm or less in yet other embodiments, where each of the above weight fractions or ppm is on a weight basis. In other embodiments, benzene may not be present at detectable limits in the recovered overheads fraction.

In other embodiments, such as where water and any unreacted alcohols or ethers are separated from the $C_6$ and lighter hydrocarbons, the benzene content of the recovered $C_6$ and lighter hydrocarbon fraction may be 0.5 percent or less, by weight, in some embodiments. In other embodiments, the benzene content of the recovered $C_6$ and lighter hydrocarbon fraction may be 0.25 percent or less; 1000 ppm or less in other embodiments; 100 ppm or less in other embodiments; and 10 ppm or less in yet other embodiments. In other embodiments, benzene may not be present in the recovered $C_6$ and lighter hydrocarbon fraction at detectable limits. Benzene concentration in the bottoms fraction recovered from the catalytic distillation column will also be minimal or zero.

As described above, processes disclosed herein may include various feeds, including gasoline fractions, ethers and alcohols, as well as alkylation catalysts. These will each be described below in further detail.

Gasoline Fraction

It may be desirable to reduce or remove benzene in any number of refinery streams. As used herein, a "gasoline fraction" includes individual refinery streams suitable for use as a blend stock for gasoline, or a blended gasoline stream formed by blending two or more streams, each of which are suitable for use as a gasoline blend stock. A suitable gasoline blend stock, when blended with other refinery streams, produces a combined stream which meets the requirements for gasoline, which requirements are well documented in Federal and State regulations.

The hydrocarbon feed to the processes disclosed herein may be a benzene-containing gasoline fraction which boils in the gasoline boiling range, including reformate, FCC gasoline, coker pentane/hexane, coker naphtha, FCC naphtha, straight run gasoline, pyrolysis gasoline, coal oven naphtha, and mixtures containing two or more of these streams. In some embodiments, reformate streams may be undistilled, such as a reformate stream fed directly from a reformer to processes described herein. Such gasoline fractions typically have a normal boiling point within the range of 0° C. and 260° C., as determined by an ASTM D86 distillation. Feeds of this type include light naphthas typically having a boiling range of about $C_6$ to 165° C. (330° F.); full range naphthas, typically having a boiling range of about $C_5$ to 215° C. (420° F.), heavier naphtha fractions boiling in the range of about 125° C. to 210° C. (260° F. to 412° F.), or heavy gasoline fractions boiling in the range of about 165° C. to 260° C. (330° F. to 500° F.). In general, a gasoline fuel will distill over the range of from about room temperature to 260° C. (500° F.). In some embodiments, these streams may be treated to remove sulfur, nitrogen, and other undesired components.

Gasoline fractions for use in embodiments of the alkylation processes described herein may include $C_3$ to $C_9$ and higher hydrocarbons. For example, refinery streams may be separated by fractional distillation, recovering a certain fraction for further processing. A light naphtha cut is one such refinery stream, and because such a cut often contains compounds that are very close in boiling points, the separations are not precise. The light naphtha refinery cut is valuable as a source of isoolefins ($iC_5=$ and $iC_6=$compounds, for example) for forming an ether by reaction with ethanol. Thus, a $C_5$ stream, for instance, may include $C_4$ s and up to $C_8$s and higher. These components may be saturated (alkanes), unsaturated (mono-olefins, including isoolefins), and poly-unsaturated (diolefins, for example). Additionally, the components may be any or all of the various isomers of the individual compounds. Such a mixture may easily contain 150 to 200 components. Other hydrocarbon streams of $C_4$ to $C_9$ carbon atoms may be used in embodiments disclosed herein.

In some embodiments, gasoline fractions may include a $C_4$ cut, which may include $C_3$ to $C_5$ or higher hydrocarbons (i.e., $C_{6+}$). In other embodiments, gasoline fractions may include a $C_5$ cut, which may include $C_4$ to $C_8$ or higher hydrocarbons, including olefins. In other embodiments, gasoline fractions may include a $C_6$ cut, which may include $C_4$ to $C_9$ or higher hydrocarbons, including olefins. In other various embodiments, gasoline fractions may include mixtures of one or more of $C_4$, $C_5$, $C_6$, and $C_{7+}$ hydrocarbons, where the mixture includes olefinic compounds. The above described streams may include $C_4$ to $C_7$ streams, FCC gasoline, coker gasoline, and other refinery streams having similar properties.

Saturated compounds included in the above described gasoline fractions may include various isomers of butane, various isomers of pentane, and various isomers of hexane, among others, for example. Olefinic compounds included in the above described gasoline fractions may include isobutylene and other butene isomers, various isomers of pentene, various isomers of hexene, and various isomers of heptene, among others, for example. Aromatic compounds that may be included in the above described gasoline fractions may include benzene, toluene, xylenes, ethylbenzene, cumenes, and other various derivatives of benzene, such as polyalkylated benzene (ethyl methyl benzene, diethyl benzene, etc.).

Alcohols

Alcohols useful in embodiments disclosed herein may include $C_1$ to $C_6$ primary and secondary alcohols. The term "alcohol" includes lower alkyl alcohols capable of forming azeotropes with the saturated and unsaturated hydrocarbons, in particular the $C_3$ to $C_7$ hydrocarbons, of the hydrocarbon feedstock. Examples of alcohols useful in embodiments disclosed herein include methanol, ethanol, n-propanol, i-propanol, n-butanol, i-butanol and t-butanol. In some embodiments, methanol may be used in combination with one or more of the $C_{2+}$ alcohols.

In some embodiments, the alcohols useful in embodiments disclosed herein may include bio-ethanol. Bio-ethanol is a feed material that may be derived from renewable resources, such as corn, sugarcane, or lignocellulose. While direct blending of alcohol into gasoline may be performed by simple mixing, the vapor pressure of the gasoline is increased due to the non-ideal thermodynamic interactions of the alcohol and hydrocarbons. Use of bio-ethanol according to embodiments disclosed herein may provide an alternative method to incorporate a renewable resource, bio-ethanol, as a gasoline feed stock, without the undesirable increase in gasoline vapor pressure.

Ethers

Ethers useful in embodiments disclosed herein may include dimethyl ether, diethyl ether, dipropyl ether, diisopropyl ether, dibutyl ether, di tert-butyl ether, as well as mixed ethers such as methyl ethyl ether, methyl propyl ether, methyl butyl ether, ethyl propyl ether, ethyl isopropyl ether, ethyl butyl ether, propyl butyl ether, as well as the sec- and tert-forms of the ethers, such as methyl tert-butyl ether (MTBE), methyl sec-butyl ether (MSBE), ethyl tert-butyl ether (ETBE), and other ethers as known in the art.

Alkylation Catalysts

Any catalyst useful for the alkylation of benzene with an alcohol may be used in the processes disclosed herein. For example, molecular sieves or zeolitic catalysts may be useful for the alkylation of benzene. Molecular sieves useful in embodiments disclosed herein may include porous, crystalline, three-dimensional alumina-silicates of the zeolite mineral group. The crystal skeleton is composed of silicon and aluminum atoms each surrounded by four oxygen atoms to form. The term molecular sieve can be applied to both naturally occurring zeolites and synthetic zeolites. Naturally occurring zeolites have irregular pore size and are not generally considered as equivalent to synthetic zeolites. Amorphous forms of synthetic silicas and aluminas may also be used.

Synthetic zeolites are typically prepared in the sodium form, wherein a sodium cation is in close proximity to each aluminum tetrahedron and thereby balancing its charge. To date, seven principal types of molecular sieves have been reported, namely A, X, Y, L, erionite, omega and mordenite. The type A zeolite has relatively small effective pore size (diameter). Types X and Y have larger pore size and differ with regard to the ratio of $Al_2O_3$ to $SiO_2$. The type L zeolite has a higher ratio of $Al_2O_3$ to $SiO_2$.

In a family of embodiments, catalysts useful in the alkylation processes disclosed herein may contain a zeolite sometimes referred to as medium pore or ZSM-5 type. In other embodiments, the zeolite may be a medium pore shape selective acidic metallosilicate zeolite selected from the group consisting of ZSM-5, H-ZSM-5, ZSM-11, ZSM-12, ZSM-22, ZSM-23, ZSM-35, ZSM-50, MCM-22, as well as larger pore zeolite Y and zeolite Beta. In a family of embodiments, a particular catalyst found to effectively facilitate alkylation of benzene is zeolite beta in proton form.

Other catalysts useful in embodiments disclosed herein may include phosphorous-modified zeolites, aluminas, and silicas. For example, one particular catalyst useful in embodiments disclosed herein is $AlPO_4$. In another embodiment, the $AlPO_4$ may be supported on alumina.

To facilitate fractionation and catalytic activity, the above described catalysts may be prepared in the form of a distillation structure. The catalytic distillation structure must be able to function as catalyst and as mass transfer medium. The catalyst must be suitably supported and spaced within the column to act as a catalytic distillation structure.

In some embodiments, the catalyst is contained in a structure as disclosed in U.S. Pat. No. 5,730,843, which is hereby incorporated by reference. In other embodiments, one or more of the above-described catalysts may be contained in a plurality of wire mesh tubes closed at either end and laid across a sheet of wire mesh fabric such as demister wire. The sheet and tubes are then rolled into a bale for loading into the distillation column reactor. This embodiment is described, for example, in U.S. Pat. No. 5,431,890, which is hereby incorporated by reference. Other useful catalytic distillation structures are disclosed in U.S. Pat. Nos. 4,302,356, 4,443,559, 4,731,229, 5,073,236, 5,431,890, 5,266,546, and 5,730,843, which are each incorporated by reference.

Referring now to FIG. 1, a simplified process flow diagram for the selective alkylation of benzene according to embodiments herein is illustrated. Alcohol/ether and a benzene-containing gasoline fraction may be fed via flow lines 6 and 8, respectively, to catalytic distillation column 10. Catalytic distillation column 10 may include one or more reaction zones 12, containing an alkylation catalyst, located in an upper portion of distillation column 10.

Gasoline fraction feed line 8 should be fed to distillation column reactor 10 at a location below reaction zone 12. The alcohol/ether may be fed above, below, or within reaction zone 12. When each of the feeds is located below reaction zone 12, for example, the alcohol/ether and the $C_6$ and lighter hydrocarbons, including benzene, may be distilled upward in the column, and $C_7$ and heavier components may be distilled downward, thus avoiding or minimizing contact of toluene and other high octane components with the alkylation catalyst.

Benzene and alcohol/ether may react in reaction zone 12 to form an alkylate product and water. Alcohol may also be formed during alkylation with ether feeds, as noted above; ethers may also be formed as a byproduct during alkylation with alcohol feeds. The alkylate product will distill downward in the column along with the $C_{7+}$ hydrocarbons, and may be recovered as a bottoms fraction via flow line 14. Water, $C_6$ and lighter hydrocarbons, as well as any unreacted and/or byproduct ethers and alcohols or benzene may be recovered as an overheads fraction via flow line 16.

The overheads fraction in line 16 may be at least partially condensed and separated in overhead drum 18. If desired, overhead drum 18 may include partitions or other means for separation of water and the $C_6$ and lighter hydrocarbons. The water-rich fraction (i.e., greater than 50% water) may be recovered from overhead drum 18 via flow line 20. A hydrocarbon-rich fraction (i.e., greater than 50 weight percent hydrocarbon) may be recovered via flow line 22. A portion of the hydrocarbon-rich fraction may be fed as reflux to catalytic distillation column 10 via flow line 23. The remaining portion of the hydrocarbon-rich fraction may be further separated to recover the hydrocarbons and any unreacted and/or byproduct alcohols and ethers.

In some embodiments, the hydrocarbon-rich fraction may be fed via flow line 22 to a water-wash column 24. Unreacted alcohol and ether and additional water may be removed from the $C_6$ and lighter hydrocarbons by contact of with water fed to water-wash column 24 via flow line 26. The $C_6$ and lighter hydrocarbons, having a reduced alcohol and water content, may be recovered from water-wash column 24 via flow line 28. The wash water and alcohol may be recovered from water-wash column 24 via flow line 30.

The water, ethers, and alcohol recovered via flow line 30 may then be separated, such as by fractionation in distillation column 32. As illustrated for the separation of water and a lighter alcohol, a water-rich fraction may be recovered from distillation column 32 via flow line 34, a portion of which may be used as wash water fed to water-wash column 24 via flow line 26. An alcohol-rich fraction may be recovered from distillation column 32 via flow line 36, a portion of which may be recycled as alcohol feed to catalytic distillation column 10 via flow line 38 in some embodiments.

The hydrocarbons recovered via flow lines 14 and 28 may be used as gasoline blend stocks. For example, one or more of the $C_6$ and lighter fraction recovered via flow line 28 and the $C_7$ and heavier fraction recovered via flow line 14 may be used as a low benzene content gasoline blend stock, for combination with other gasoline blend stocks present in a refinery or blending unit. In other embodiments, the fractions in flow lines 14 and 28 may be combined for use as a gasoline or a gasoline blendstock.

In some embodiments, it may be desirable to add a small amount of hydrogen to catalytic distillation column 10. For example, hydrogen may be advantageously used to prolong the service life of the alkylation catalyst contained in reaction zone 12. Any unreacted hydrogen passing through the column may be vented from overhead drum 18 via flow line 42, if necessary.

As another alternative, water may be recovered directly from catalytic distillation column 10. For example, a water-rich fraction may be recovered from catalytic distillation column 10 via a side draw 44.

As described above with respect to FIG. 1, selective alkylation of benzene may be achieved via fractionation of $C_7$ and heavier components from $C_6$ and lighter components. Gasoline fractions used as feeds to the processes described herein may include any number of hydrocarbons, where the lightest hydrocarbons may include C3, C4, C5, and/or C6 compounds. The operation of catalytic distillation column 10 and the separations downstream of catalytic distillation column 10 may be adjusted to account for the various feeds. For example, pressures, temperatures, and other operating conditions may be adjusted to achieve the desired $C_6/C_7$ split to avoid contact of the $C_7$ compounds with the alkylation catalyst. In other embodiments, such as where it is desired to at least partially alkylate toluene, catalytic distillation column 10 operating conditions may be adjusted to achieve the desired contact of the $C_7$ components with the alkylation catalyst.

The aforementioned separations may be further complicated by azeotropes that may form between water, ethers, and alcohols used in the alkylation process, as well as those that may form between hydrocarbons and water, alcohols, and ethers. Embodiments disclosed herein may be limited in the separations achieved by such azeotropes. Alternatively, embodiments disclosed herein may also include more rigorous separation schemes so as to break the azeotropes and recover hydrocarbon, alcohol, ethers, or water streams having a higher purity than attainable through basic separations.

EXAMPLES

Examples 1, 2 and 3 are carried out in a one inch diameter column including three sections (two 10-foot sections and a top 5-foot section). The reboiler is located at the bottom of the tower. Alcohol is fed to first section of the tower at 66 inches above the reboiler. Benzene is fed to the unit approximately one foot above the alcohol feed. Catalyst modules are located in the middle (a 10-foot) section. The top 5-foot section is empty. An overhead stream is taken out of the top of the column via an overhead condenser. A bottom stream is drawn from the reboiler. The benzene feed and reflux are each heated before entering the column. Alcohol is fed straight to the column without being heated.

Example 1

Benzene and ethanol are fed to the tower operating at 200 psig overhead pressure. Approximately 0.22 lb (or 100 g) of ZEOLYST Beta catalyst is used, where the catalyst is loaded into ten 6 inch height by 1 inch diameter bales, each containing 10 g of catalyst. Approximately 24 inches of saddles is located above the catalyst, no packing material is located below the catalyst bed. Benzene feed is 99.9% pure, and the ethanol feed is 98% pure, each by weight. Feed flow rates are 1.0 lb/hr for benzene and 0.3 lb/hr for ethanol, reflux is set at 2.3 lb/hr. The overhead flow rate is 0.9 lb/hr and the bottoms flow rate is 0.4 lb/hr.

Analysis of the composition of the overhead stream reveals 82% benzene, 7% ethanol, 9% diethyl ether (undesired product), and light hydrocarbons forming the remainder, each by weight. The bottom stream contains 60% benzene, 36% ethylbenzene (desired product) and 3% diethylbenzene (poly-alkylated by-product) plus some heavies, each by weight. Overall conversion of benzene to ethylbenzene is 11% (mole).

Example 2

Benzene and ethanol are fed to the tower operating at 200 psig. Approximately 0.25 lb (or 112 g) of Lummus Technology High Performance Beta CP759A catalyst is used, where the catalyst is loaded into ten 6 inch height by 1 inch diameter bales, each containing 11 g of catalyst. Approximately 24 inches of saddles is located above the catalyst, no packing material is located below the catalyst bed. Benzene feed is 99.9% pure, ethanol feed is 97% pure, each by weight. Feed flow rates are 1.0 lb/hr for benzene and 0.3 lb/hr for ethanol, and reflux is set at 3.4 lb/hr. The overhead flow rate is 0.7 lb/hr and the bottoms flow rate is 0.5 lb/hr.

Analysis of the composition of the overhead stream reveals 88% benzene, 7% ethanol, 5% diethyl ether (undesired product) and light hydrocarbons forming the remainder, each by weight. The bottom stream contains 34% benzene, 57% ethylbenzene (desired product) and 9% diethylbenzene (poly-alkylated by-product), plus some heavies, each by weight. Overall conversion of benzene to ethylbenzene is 22% (mole).

Example 3

Benzene and isopropanol are fed to the tower operating at 200 psig. Approximately 0.25 lb (or 112 g) of Lummus Technology High Performance Beta CP759A catalyst is used, where the catalyst is loaded into ten 6 inch height by 1 inch diameter bales, each containing 11 g of catalyst. Approximately 24 inches of saddles is located above the catalyst, and approximately 78 inches of saddles located below the catalyst bed. Benzene feed is 99.9% pure, and isopropanol feed is 97% pure. Feed flow rates are 0.5 lb/hr for benzene and 0.7 lb/hr for isopropanol. Reflux is set at 4.5 lb/hr. The overhead flow rate is 0.5 lb/hr and the bottoms flow rate is 0.5 lb/hr, where the net mass balance includes some light gases being vented.

Analysis of the composition of the overhead stream reveals 76% benzene, 21% isopropanol, about 1% diisopropyl ether, with the remainder including other light hydrocarbons, each by weight. The bottom stream contains 17% benzene, 64% cumene (desired product) and 19% diisopropylbenzene (poly-alkylated by-product), plus heavies, each by weight. Overall conversion of benzene to cumene is 44% (mole).

Example 4

Benzene and diethyl ether are fed to the tower operating at 200 psig. Approximately 0.25 lb (or 112 g) of Lummus Technology High Performance Beta CP759A catalyst is used, where the catalyst is loaded into ten 6 inch height by 1 inch diameter bales, each containing 11 g of catalyst. Approximately 24 inches of saddles is located above the catalyst, and approximately 78 inches of saddles located below the catalyst bed. Benzene feed is 99.9% pure and diethyl ether feed was 99.8% pure. Feed flow rates are 1.0 lb/hr for benzene and 0.3 lb/hr for diethyl ether. Reflux is set at 5.0 lb/hr. The overhead flow rate is 0.5 lb/hr and the bottoms flow rate is 0.8 lb/hr, where the net mass balance includes some light gases being vented.

Analysis of the composition of the overhead stream reveals 78% benzene, 20% diethyl ether, about 2% of ethanol. The bottoms stream contains about 45% benzene, 43% ethylbenzene (desired product) and 12% diethylbenzene (poly-alkylated by-product). Overall conversion of benzene to ethylbenzene is 25% (mole).

While the examples above included a benzene feed, one skilled in the art can readily appreciate that benzene contained in a mixed hydrocarbon stream would likewise be alkylated when contacted with an alcohol or an ether in the presence of an alkylation catalyst.

As described above, embodiments described herein may provide for the selective alkylation of benzene, resulting in hydrocarbon streams having a reduced or nil benzene concentration. The resulting low benzene content streams may be used as gasoline or gasoline blend stocks to result in gasolines meeting the increasingly stringent requirements for benzene imposed by various governments.

Advantageously, embodiments disclosed herein may provide an economical alternative to costly extraction or hydrogenation of benzene from various gasoline fractions, including reformate. Additionally, embodiments disclosed herein may result in gasoline fractions having an improved octane value. Other embodiments disclosed herein advantageously provide a route for the introduction of a renewable resource, bio-ethanol, into gasoline, without the increase in vapor pressure encountered for mere blending of ethanol and gasoline.

While the disclosure includes a limited number of embodiments, those skilled in the art, having benefit of this disclosure, will appreciate that other embodiments may be devised which do not depart from the scope of the present disclosure. Accordingly, the scope should be limited only by the attached claims.

What is claimed is:
1. A process for the reduction of benzene in a gasoline stream, the process comprising:
feeding a gasoline fraction comprising benzene and $C_6+$ hydrocarbons and at least one of an alcohol and an ether to a catalytic distillation column comprising at least one reaction zone containing an alkylation catalyst, wherein the at least one reaction zone is above a gasoline fraction feed location,
concurrently in the catalytic distillation column:
separating the $C_6$ hydrocarbons from $C_{7+}$ hydrocarbons, wherein the $C_6$ hydrocarbons and benzene distill upward into the at least one reaction zone;
contacting benzene and the at least one of an alcohol and an ether in the at least one reaction zone in the presence of the alkylation catalyst to convert at least a portion of the benzene and the at least one of an alcohol and an ether to an alkylate;
recovering an overheads fraction comprising $C_6$ hydrocarbons, any unreacted alcohol and ether, and water; and
recovering a bottoms fraction comprising $C_{7+}$ hydrocarbons and the alkylate,
wherein the catalytic distillation column is operated to avoid contact of $C_{7+}$ aromatic compounds with the alkylation catalyst.

2. The process of claim 1, wherein the alcohol comprises at least one of methanol, ethanol, propanol, and isopropanol.

3. The process of claim 1, wherein the ether comprises at least one of dimethyl ether, diethyl ether, dipropyl ether, diisopropyl ether, dibutyl ether, di tert-butyl ether, methyl ethyl ether, methyl propyl ether, methyl butyl ether, ethyl propyl ether, ethyl isopropyl ether, ethyl butyl ether, propyl butyl ether, methyl tert-butyl ether (MTBE), methyl sec-butyl ether (MSBE), and ethyl tert-butyl ether (ETBE).

4. The process of claim 1, wherein the alkylation catalyst comprises at least one of H-ZSM-5, beta zeolite in proton form, $AlPO_4$, and alumina supported $AlPO_4$.

5. The process of claim 4, wherein the catalyst is prepared as a distillation structure.

6. The process of claim 1, further comprising maintaining the at least one reaction zone at a temperature in the range from about 300° F. to 600° F.

7. The process of claim 1, wherein the gasoline fraction comprises undistilled reformate.

8. The process of claim 1, wherein the gasoline fraction comprises at least one of reformate, a $C_{4+}$ gasoline fraction, a $C_{5+}$ gasoline fraction, and a $C_{6+}$ gasoline fraction.

9. The process of claim 1, further comprising feeding hydrogen to the catalytic distillation column below the at least one reaction zone.

10. The process of claim 1, further comprising recovering a water-rich fraction as a side draw from the catalytic distillation column.

11. The process of claim 1, further comprising:
condensing at least a portion of the overhead fraction in an overhead system;
recovering a water-rich phase and a hydrocarbon-rich phase comprising the $C_6$ hydrocarbons.

12. The process of claim 11, wherein the hydrocarbon-rich phase further comprises unreacted alcohol or ether, the process further comprising:
water washing the hydrocarbon-rich phase to separate the $C_6$ hydrocarbons from the unreacted alcohol and ether; and
recovering a $C_6$ hydrocarbon fraction; and
recovering a wash fraction comprising water and the unreacted alcohol and ether.

13. The process of claim 12, further comprising separating the wash fraction to recover a water-rich fraction and a fraction comprising the alcohol and/or ether.

14. The process of claim 13, further comprising recycling at least a portion of the fraction comprising alcohol and/or ether to the catalytic distillation column as an additional alcohol/ether feed.

15. The process of claim 13, further comprising recycling at least a portion of the water-rich fraction to the water washing.

16. The process of claim 1, wherein a mole ratio of the at least one of an alcohol and an ether to benzene in the feed is in the range from 0.5:1 to 5:1.

17. The process of claim 1, wherein a concentration of benzene in the overheads fraction is less than 100 ppm, by weight.

18. The process of claim 12, wherein a concentration of benzene in the $C_6$ hydrocarbon fraction is less than 100 ppm, by weight.

19. The process of claim 12, further comprising using at least one of the bottoms fraction and the $C_6$ hydrocarbon fraction as a gasoline blend stock.

* * * * *